(12) United States Patent
Tahmasebi Maraghoosh et al.

(10) Patent No.: US 11,071,518 B2
(45) Date of Patent: Jul. 27, 2021

(54) IMAGING APPARATUS FOR BIOPSY OR BRACHYTHERAPY

(71) Applicant: KONINKLIJKE PHILIPS N.V., Eindhoven (NL)

(72) Inventors: Amir Mohammad Tahmasebi Maraghoosh, Ridgefield, CT (US); Shyam Bharat, Arlington, MA (US); Ameet Kumar Jain, New York, NY (US); Francois Guy Gerard Marie Vignon, Croton on Hudson, NY (US); Ehsan Dehghan Marvast, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1569 days.

(21) Appl. No.: 14/903,288

(22) PCT Filed: Jun. 24, 2014

(86) PCT No.: PCT/EP2014/063200
§ 371 (c)(1),
(2) Date: Jan. 7, 2016

(87) PCT Pub. No.: WO2015/003895
PCT Pub. Date: Jan. 15, 2015

(65) Prior Publication Data
US 2016/0143615 A1    May 26, 2016

Related U.S. Application Data

(60) Provisional application No. 61/843,665, filed on Jul. 8, 2013.

(30) Foreign Application Priority Data

Aug. 1, 2013 (EP) .................................... 13178918

(51) Int. Cl.
*A61B 8/08* (2006.01)
*A61B 8/00* (2006.01)
(Continued)

(52) U.S. Cl.
CPC ............ *A61B 8/0841* (2013.01); *A61B 8/085* (2013.01); *A61B 8/12* (2013.01); *A61B 8/4245* (2013.01);
(Continued)

(58) Field of Classification Search
CPC ......... A61B 8/0841; A61B 8/085; A61B 8/12; A61B 8/463; A61B 8/466; A61B 8/483;
(Continued)

(56) References Cited

U.S. PATENT DOCUMENTS 6,246,898 B1   6/2001   Vesely et al.
7,713,210 B2   5/2010   Byrd et al.
(Continued)

OTHER PUBLICATIONS

Mung, J. et al., "A non-disruptive technology for robust 3D tool tracking for ultrasound-guided interventions", Medical Image Computing and Computer Assisted Intervention, 2011, Abstract.

*Primary Examiner* — Jeffrey G Hoekstra
*Assistant Examiner* — Katherine M McDonald
(74) *Attorney, Agent, or Firm* — Sherry Austin (57) ABSTRACT

An imaging apparatus (24) images an introduction element (17) like a needle or a catheter for performing a biopsy or a brachytherapy. The introduction element (17) includes at least one ultrasound receiver (21) arranged at a known location. An ultrasound probe (12) for being inserted into a living being (2) emits ultrasound signals for acquiring ultrasound data of an inner part (19) of the living being (2). A first tracking unit (3) tracks the location of the introduction element (17) based on a reception of the emitted ultrasound signals by the at least one ultrasound receiver (21). An (Continued)

imaging unit (4) generates an indicator image showing the inner part (19) and an indicator of the introduction element (17) based on the tracked location. A display (5) displays the indicator image providing feedback about the location of the introduction element (17).

8 Claims, 3 Drawing Sheets (51) Int. Cl.
*A61B 8/12* (2006.01)
*A61N 5/10* (2006.01)
*A61B 17/34* (2006.01)
*A61B 34/20* (2016.01)
*A61B 5/06* (2006.01)
*A61B 90/00* (2016.01)
*A61B 34/10* (2016.01)
*A61B 10/04* (2006.01)

(52) U.S. Cl.
CPC .............. *A61B 8/463* (2013.01); *A61B 8/466* (2013.01); *A61B 8/483* (2013.01); *A61B 8/5207* (2013.01); *A61B 17/3403* (2013.01); *A61B 34/20* (2016.02); *A61N 5/1001* (2013.01); *A61N 5/1002* (2013.01); *A61N 5/1027* (2013.01); *A61N 5/1039* (2013.01); *A61B 5/06* (2013.01); *A61B 8/4461* (2013.01); *A61B 8/5261* (2013.01); *A61B 2010/045* (2013.01); *A61B 2017/3413* (2013.01); *A61B 2034/107* (2016.02); *A61B 2034/2051* (2016.02); *A61B 2090/3786* (2016.02); *A61B 2090/3788* (2016.02); *A61N 2005/1058* (2013.01)

(58) Field of Classification Search
CPC ............ A61B 8/5207; A61B 2010/045; A61N 5/1002; A61N 5/1027; A61N 5/1039
See application file for complete search history.

(56) References Cited

U.S. PATENT DOCUMENTS

| | | |
|---|---|---|
| 8,548,562 B2 | 10/2013 | Trachtenberg |
| 8,792,962 B2 | 7/2014 | Esguerra et al. |
| 8,926,528 B2 | 1/2015 | Govari |
| 9,585,628 B2 | 3/2017 | Vignon et al. |
| 2003/0135115 A1 | 7/2003 | Burdette et al. |
| 2003/0231789 A1 | 12/2003 | Parker et al. |
| 2005/0182316 A1 | 8/2005 | Burdette et al. |
| 2009/0287223 A1 | 11/2009 | Pua et al. |
| 2010/0016710 A1 | 1/2010 | Kumar et al. |
| 2012/0172458 A1 | 7/2012 | Onishi |
| 2013/0041252 A1 | 2/2013 | Vignon et al. |
| 2014/0094695 A1 | 4/2014 | Jain et al. |
| 2015/0297114 A1 | 10/2015 | Bard |

FIG. 4

IMAGING APPARATUS FOR BIOPSY OR BRACHYTHERAPY

CROSS-REFERENCE TO PRIOR APPLICATIONS

This application is the U.S. National Phase application under 35 U.S.C. § 371 of International Application Serial No. PCT/EP2014/063200, filed on Jun. 24, 2014, which claims the benefit of U.S. Application Ser. No. 61/843,665, filed on Jul. 8, 2013 and European Application No. 13178918.2 filed on Aug. 1, 2013. These applications are hereby incorporated by reference herein.

FIELD OF THE INVENTION

The present invention relates to an imaging apparatus, an imaging method, and an imaging computer program for imaging an introduction element like a needle or a catheter within a living being during a biopsy or a brachytherapy. The present invention relates further to a system for performing a biopsy or a brachytherapy comprising the imaging apparatus.

BACKGROUND OF THE INVENTION

WO 2012/172458 A1 discloses an imaging system comprising a medical device having a tracking element mounted thereon and an array of transducers spaced apart from one another for exchanging energy in a subject between the tracking element and the array of transducers. The imaging system further comprises a trilateration module configured to interpret signals sensed between the tracking element and the array of transducers, in order to compute time-of-flight signals associated with the transducers in the array, wherein based on the time-of-flight signals the position of the tracking element is determined. This position is then used to locate the position of the medical device in a visual image.

US 2013/0041252 A1 discloses an ultrasound receive beamformer comprising a retrospective dynamic transmit focusing receive beamformer for one-way only beamforming of transmissive ultrasound. The beamformer is operable to process signals output by a receiver of the transmissive ultrasound, wherein the transmissive ultrasound comprises transmissive ultrasound issued by synthetic aperture acquisition with a virtual transducer array made of virtual transducer array elements. Each virtual transducer array element comprises a focal location of one focused beam emanating from a real imaging array.

WO 2008/063249 A2 discloses a robotic surgical system for use in laparoscopic procedures. The robotic surgical system comprises a realtime 3D ultrasound probe, a realtime 3D scanner coupled to the probe, wherein the scanner scans a volume and generates an output, and a surgical robot coupled to the realtime 3D scanner, wherein the surgical robot automatically performs an aspect of a surgical procedure in response to the scanner output.

U.S. Pat. No. 6,246,898 B1 discloses an apparatus for performing an in vivo medical procedure on an associated body. The apparatus comprises a mobile transducer mounted to a catheter including a lumen, a plurality of reference transducers mounted to locations on the body, wherein the plurality of reference transducers are distributed at positions substantially surrounding the body, and a means for energizing the mobile transducer and the plurality of reference transducers such that at least one respective transducer generates a positional signal and at least another respective transducer detects the positional signal, in order to measure time-of-flight of the positional signal. The apparatus further comprises means for sequentially varying the energizing of the mobile transducer and the plurality of reference transducers according to a duty cycle such that each transducer alternates between transmit and receive modes over the course of the duty cycle and 3D generating means for generating three-dimensional coordinates of the mobile transducer relating to a reference frame established by the plurality of reference transducers. Moreover, the apparatus comprises a display means for generating a display indicative of a positional path followed by the catheter, a needle extendable from a tip of the catheter, and a control means for extending the needle from the tip of the catheter and initiating a flow of fluid from the needle.

US 2010/0016710 A1 discloses an image acquisition system used for performing a prostate biopsy under transrectal ultrasound guidance. The image acquisition system comprises an ultrasound probe attached to a biopsy needle assembly to be inserted into the rectum of a person. The ultrasound probe with the biopsy needle assembly is held by a robotic arm, wherein the position of the robotic arm is determined by using a set of position sensors. Since the position of the ultrasound probe is known due to the position of the robotic arm, which holds the ultrasound probe, ultrasound images generated by using the ultrasound probe while the ultrasound probe was at different positions can be combined to generate an overall ultrasound image, especially a three-dimensional ultrasound image, which is used to determine the surface of the prostate. The surface of the prostate is shown on a display together with a model of the biopsy needle, in order to show the location of the biopsy needle relative to the prostate.

Today, prostate cancer is the most common organ malignancy among American men and performing a prostate biopsy under transrectal ultrasound (TRUS) imaging guidance is the most common clinical practice for prostate cancer diagnosis. In this procedure, an introduction element like a needle is introduced into a man's rectum and small samples are extracted from his prostate in order to be tested for the presence of cancer. The extraction is performed using ultrasound images from a transrectal ultrasound probe for guidance. However, while the use of ultrasound is very attractive in clinical care due to its low cost, ease of use, excellent soft tissue visualization, and lack of ionizing radiation, it is not well suited for imaging clinical tools, such as a needle or a catheter, which are typically made of hard materials such as metal or plastic that are practically invisible for ultrasound. Due to this "invisible tool" phenomenon, it is difficult for a physician performing a prostate biopsy to accurately navigate the needle or another introduction element to the site of the prostate where the biopsy shall be performed and, correspondingly, it is also difficult to determine the true site of the prostate where a sample was taken.

SUMMARY OF THE INVENTION

It is an object of the present invention to provide an imaging apparatus, an imaging method, and an imaging computer program for imaging an introduction element within a living being during a biopsy or a brachytherapy, which allows receiving a feedback about the location of the introduction element within the living being.

In a first aspect of the present invention, an imaging apparatus for imaging an introduction element within a living being is presented, wherein the introduction element is adapted to be inserted into the living being for performing a biopsy of an inner part of the living being or for introducing a radiation source into or next to the inner part of the living being for performing a brachytherapy, wherein the introduction element comprises at least one ultrasound receiver arranged at a known location of the introduction element, wherein the imaging apparatus comprises:

an ultrasound probe for being inserted into the living being, wherein the ultrasound probe is adapted to emit ultrasound signals for acquiring ultrasound data of the inner part of the living being, a first tracking unit for tracking the location of the introduction element within the living being based on a reception of the emitted ultrasound signals by the at least one ultrasound receiver, an image providing unit for providing a pre-interventional image showing the inner part of the living being, which indicates a diseased condition of the inner part of the living being, an imaging unit for generating an indicator image showing the inner part of the living being and an indicator of the introduction element, based on the tracked location of the introduction element, wherein the imaging unit is adapted to generate an ultrasound image showing the inner part of the living being based on the acquired ultrasound data and to register the pre-interventional image with the ultrasound image, wherein the imaging unit is adapted to generate the indicator such that it represents the ultrasound image or the registered pre-interventional image or a fused image of the ultrasound image and the registered pre-interventional image, wherein a site where the biopsy was performed or where the radiation source was introduced by means of the introduction element is indicated in the indicator image, and a display for displaying the indicator image.

Since the location of the introduction element within the living being, which may be a human or an animal, is tracked by the first tracking unit and since the imaging unit generates an indicator image showing the inner part of the living being and an indicator of the introduction element based on the tracked location of the introduction element, wherein the generated indicator image is finally displayed on a display, during or after the biopsy or the brachytherapy, a user like a physician navigating the introduction element can receive a feedback about the location of the introduction element within the living being. For example, the imaging unit can be adapted to update the generated indicator image in real-time during the biopsy or the brachytherapy based on the tracked location of the introduction element, wherein the display can be adapted to display the updated indicator image in real-time. In this case, since the user can receive a real-time feedback about the location of the introduction element within the living being from the indicator image, he/she can more accurately navigate the introduction element to the site of the inner part of the living where the biopsy shall be performed or where the radiation source shall be introduced.

In addition, since the imaging apparatus comprises an ultrasound probe for being inserted into the living being, wherein the ultrasound probe emits ultrasound signals for acquiring ultrasound data of the inner part of the living being, and since the first tracking unit tracks the location of the introduction element within the living being based on the reception of the emitted ultrasound signals by the at least one ultrasound receiver, i.e., since the acquisition of the ultrasound data and the tracking of the location of the introduction element are based on the same ultrasound signals, the tracked location of the introduction element can be determined in the same coordinate frame as the ultrasound data, which can allow for a very robust, bias-free tracking.

The introduction element is preferentially a needle or a catheter to be inserted under ultrasound image guidance, wherein the introduction element is preferentially adapted to perform a biopsy of the inner part of the living being and/or to perform a brachytherapy by introducing a radiation source, such as a radioactive radiation source, into or next to the inner part of the living being. The inner part of the living being is preferentially the prostate of a human, wherein the ultrasound probe is a transrectal ultrasound probe. In particular, the imaging apparatus can be adapted to image the introduction element during a prostate biopsy or during a prostate brachytherapy.

Since the at least one ultrasound receiver is arranged at a known location of the introduction element, e.g., close to or at a tip of the introduction element, the tracking can preferentially be very precise even if the introduction element is an elongated element, such as a needle or a catheter, comprising an elongated body that may bend and deflect from its original straight path. The image providing unit may be adapted to provide a 3D pre-interventional image and/or the imaging unit may be adapted to generate a 3D ultrasound image and/or a 3D indicator image.

The tracking of the location of the introduction element within the living being by the first tracking unit is preferentially based on the evaluation of the "time-of-flight" of the ultrasound signals that are emitted by the ultrasound probe and are received by the at least one ultrasound receiver.

The diseased condition can be the possible occurrence of cancer, in particular, if the inner part of the living being is the prostate of a human, prostate cancer. The pre-interventional 3D image showing the inner part of the living being is preferentially a 3D image that was generated before performing the biopsy or before performing the brachytherapy using an imaging modality that provides a better imaging of the diseased condition than ultrasound. For example, magnetic resonance imaging (MRI), in particular, magnetic resonance spectroscopy (MRS), provides an enhanced delineation of cancer compared to ultrasound and can be used to generate the pre-interventional 3D image. The pre-interventional 3D image showing the inner part of the living being can preferentially be used before performing the biopsy or before performing the brachytherapy for performing a treatment planning, i.e., for planning the site(s) where the biopsy is to be performed or where the radiation source(s) is/are to be introduced by means of the introduction element.

In an embodiment, the ultrasound image is a 3D ultrasound image and the ultrasound probe is a 2D ultrasound probe, i.e., e.g., a 1D array of ultrasound transducers, for acquiring ultrasound data of a 2D region, wherein the imaging unit is adapted to generate the 3D ultrasound image from successively acquired ultrasound data of a plurality of 2D regions using a 3D image reconstruction.

For example, it can be foreseen that the user performs a freehand sweep of the 2D ultrasound probe in order to successively acquire ultrasound data of the whole inner part of the living being, wherein the imaging unit is adapted to reconstruct the 3D ultrasound image from the ultrasound data acquired during the freehand sweep. Alternatively, it can also be foreseen that the user needs to rotate the 2D ultrasound probe around an axis directed towards the inner part of the living being in order to successively acquire sufficient ultrasound data of the inner part of the living being for allowing a 3D image reconstruction. In some embodiments, it can even be foreseen that the 2D ultrasound probe comprises driving means, e.g., comprising an electrical motor or the like, that are adapted to perform a respective sweep or rotation of the ultrasound transducers. It is noted that a 3D image reconstruction based on successively acquired ultrasound data of a plurality of 2D regions can work particularly well if the inner part of the living being is rather rigid and does not move or distort much over a short period of time. This is the case, e.g., if the inner part of the living being is the prostate of a human.

Preferentially, the imaging apparatus comprises an introduction element guide for guiding the introduction element, wherein the introduction element guide is adapted to be attached to the ultrasound probe, here, the 2D ultrasound probe, and a second tracking unit for tracking the location of the introduction element guide, wherein the imaging unit is adapted to further use the tracked location of the introduction element guide in the 3D image reconstruction. If the introduction element guide is attached to the 2D ultrasound probe and the location of the introduction element guide is tracked by the second tracking unit, e.g., during a sweep or rotation of the 2D ultrasound probe, the respective positions and orientations of the plurality of 2D regions of which the ultrasound data is successively acquired within the living being can be known from the tracked location of the introduction element guide. This information greatly simplifies the 3D image reconstruction since it indicates how the successively acquired ultrasound data is positioned resp. oriented with respect to each other. The tracking of the location of the introduction element guide by the second tracking unit may be based on an electromagnetic (EM) tracking, e.g., by making use of appropriate EM sensors mounted on the introduction element guide, or on another suitable tracking technology.

In another embodiment, the ultrasound image is a 3D ultrasound image and the ultrasound probe is a 3D ultrasound probe, i.e., e.g., a 2D array of ultrasound transducers, for acquiring ultrasound data of a 3D region, wherein the imaging unit is adapted to generate the 3D ultrasound image from the acquired ultrasound data. For example, if the 3D region of which the ultrasound data is acquired within the living being is sufficiently large, the 3D ultrasound image can preferentially be generated from a single acquisition of ultrasound data.

In an embodiment, the imaging apparatus comprises an introduction element guide for guiding the introduction element, wherein the introduction element guide is adapted to be attached to the ultrasound probe, wherein the ultrasound probe is a 2D ultrasound probe for acquiring ultrasound data of a 2D region, wherein the introduction element guide is adapted for guiding the introduction element within the 2D region, wherein the first tracking unit is adapted to track the location of the introduction element within the 2D region, wherein the imaging unit is adapted to generate as the indicator image a 2D image, wherein the 2D image is generated from the currently acquired ultrasound data, wherein the tracked location of the introduction element is indicated in the 2D image, wherein the display is adapted to display the 2D image. By generating as the indicator image a 2D image generated from the currently acquired ultrasound data, here, the ultrasound data of the 2D region that is acquired by the 2D ultrasound probe in real-time during the biopsy or the brachytherapy, wherein the tracked location of the introduction element is indicated in the 2D image, the user can receive a real-time feedback about the location of the introduction element within the living being from the indicator image. He/she can therefore more accurately navigate the introduction element to the site of the inner part of the living where the biopsy shall be performed or where the radiation source shall be introduced.

It shall be noted that the first tracking unit is preferentially able to track the location of the introduction element even when the introduction element is located slightly outside the 2D region of which the ultrasound data is acquired, e.g., if the introduction element is an elongated element, such as a needle or a catheter, comprising an elongated body that bends and deflects from its original straight path. Such "out-of-plane" tracking can be based on the effect that although the 2D ultrasound probe substantially emits ultrasound signals only within the 2D region, the ultrasound signals can nonetheless be received—albeit with a somewhat lower power—by the at least one ultrasound receiver if it is located slightly outside the 2D region. While these lower power ultrasound signals are not strong enough to generate an ultrasound image, they can be sufficient for tracking the location of the introduction element. With such "out-of-plane" tracking the indication of the tracked location of the introduction element in the indicator image may be an indication of the orthogonal projection of the tracked location of the introduction element onto the 2D region. In addition, the distance and/or side of the tracked location of the introduction element with respect to the 2D region can be indicated in the indicator image.

In an embodiment, the pre-interventional image is a pre-interventional 3D image and the imaging apparatus comprises an introduction element guide for guiding the introduction element, wherein the introduction element guide is adapted to be attached to the ultrasound probe, and a second tracking unit for tracking the location of the introduction element guide, wherein the ultrasound probe is a 2D ultrasound probe for ultrasound data of a 2D region, wherein the introduction element guide is adapted for guiding the introduction element within the 2D region, wherein the first tracking unit is adapted to track the location of the introduction element within the 2D region, wherein the imaging unit is adapted to determine a slice within the living being corresponding to the 2D region based on the tracked location of the introduction element guide and to generate as the indictor image a slice image of the determined slice, wherein the slice image is generated from the registered pre-interventional 3D image or as a fused image from the registered pre-interventional 3D image and the currently acquired ultrasound data, wherein the tracked location of the introduction element is indicated in the slice image, wherein the display is adapted to display the slice image. By generating as the indicator image a slice image of the determined slice generated from the registered pre-interventional 3D image or as a fused image from the registered pre-interventional 3D image and the currently acquired ultrasound data, here, the ultrasound data of the 2D region that is acquired by the 2D ultrasound probe in real-time during the biopsy or the brachytherapy, the user can—in addition to receiving a real-time feedback about the location of the introduction element within the living being from the indicator image— in particular also perceive the indication(s) of the diseased condition of the inner part of the living being provided by the pre-interventional 3D image. He/she can therefore even more accurately navigate the introduction element to the site of the inner part of the living where the biopsy shall be performed or where the radiation source shall be introduced. It shall be noted that also in this embodiment, an "out-of-plane" tracking as described above can be used to the same effect.

In an embodiment, the ultrasound probe is a 3D ultrasound probe for acquiring ultrasound data of a 3D region, wherein the first tracking unit is adapted to track the location of the introduction element within the 3D region, wherein the imaging unit is adapted to determine a slice within the 3D region including the tracked location of the introduction element and to generate as the indicator image a slice image of the determined slice, wherein the slice image is generated from the currently acquired ultrasound data, wherein the tracked location of the introduction element is indicated in the slice image, wherein the display is adapted to display the slice image. By generating as the indicator image a slice image generated from the currently acquired ultrasound data, here, the ultrasound data of the 3D region that is acquired by the 3D ultrasound probe in real-time during the biopsy or the brachytherapy, wherein the tracked location of the introduction element is indicated in the slice image, the user can receive a real-time feedback about the location of the introduction element within the living being from the indicator image. He/she can therefore more accurately navigate the introduction element to the site of the inner part of the living where the biopsy shall be performed or where the radiation source shall be introduced.

In an embodiment, the pre-interventional image is a pre-interventional 3D image and the imaging apparatus comprises an introduction element guide for guiding the introduction element, wherein the introduction element guide is adapted to be attached to the ultrasound probe, and a second tracking unit for tracking the location of the introduction element guide, wherein the ultrasound probe is a 3D ultrasound probe for acquiring ultrasound data of a 3D region, wherein the first tracking unit is adapted to track the location of the introduction element within the 3D region, wherein the imaging unit is adapted to determine a slice within the living being including the tracked location of the introduction element based on the tracked location of the introduction element and the tracked location of the introduction element guide and to generate as the indictor image a slice image of the determined slice, wherein the slice image is generated from the registered pre-interventional 3D image or as a fused image from the registered pre-interventional 3D image and the currently acquired ultrasound data, wherein the tracked location of the introduction element is indicated in the slice image, wherein the display is adapted to display the slice image. By generating as the indicator image a slice image of the determined slice generated from the registered pre-interventional 3D image or as a fused image from the registered pre-interventional 3D image and the currently acquired ultrasound data, here, the ultrasound data of the 3D region that is acquired by the 3D ultrasound probe in real-time during the biopsy or the brachytherapy, the user can—in addition to receiving a real-time feedback about the location of the introduction element within the living being from the indicator image—in particular also perceive the indication(s) of the diseased condition of the inner part of the living being provided by the pre-interventional 3D image. He/she can therefore even more accurately navigate the introduction element to the site of the inner part of the living where the biopsy shall be performed or where the radiation source shall be introduced.

In an embodiment, the imaging unit is adapted to generate as the indicator image a 3D image, wherein the 3D image represents the 3D ultrasound image or the registered pre-interventional 3D image or a fused image of the 3D ultrasound image and the registered pre-interventional 3D image, wherein a site where the biopsy was performed or where the radiation source was introduced by means of the introduction element is indicated in the 3D image, wherein the display is adapted to display the 3D image. This makes it possible to determine the location(s) of the site(s) where the biopsy was performed or where the radiation source(s) was/were introduced by means of the introduction element. This information can be used, e.g., for intra- and post-interventional quality control, for diagnosis, and for further treatment planning. In particular, if the 3D image generated as the indicator image represents the registered pre-interventional 3D image or a fused image of the 3D ultrasound image and the registered pre-interventional 3D image, the site(s) indicated in the 3D image can be easily correlated by the user with the indication(s) of the diseased condition of the inner part of the living being provided by the pre-interventional 3D image.

The imaging unit may be further adapted to indicate a planned site, at which a biopsy should be performed or where the radiation source should be introduced, in the indicator image. Thus, in an embodiment the planned site and the site where the biopsy was actually performed or where the radiation source was actually introduced are shown in the same indicator image, which allows for a relatively simple comparison of the actual site with the planned site, which can be used for, for instance, evaluating the quality of the biopsy or brachytherapy procedure and/or for planning further biopsy or brachytherapy steps.

In a further aspect of the present invention, a system for performing a biopsy or a brachytherapy is presented, wherein the system comprises:

an introduction element for being inserted into a living being for performing the biopsy of an inner part of the living being or for introducing a radiation source into or next to the inner part of the living being for performing the brachytherapy, wherein the introduction element comprises at least one ultrasound receiver arranged at a known location of the introduction element, and an imaging apparatus for imaging the introduction element within the living being as defined in claim 1.

If the system is adapted to perform a brachytherapy, the system can further comprise the radiation source for treating the living being. Moreover, the system may further comprise a treatment plan providing unit for providing a treatment plan indicating a planned site, at which a biopsy should be performed or where the radiation source should be introduced, wherein the imaging unit of the imaging apparatus may be adapted to indicate the planned site in the indicator image generated by the imaging unit, wherein the treatment plan providing unit may be adapted to compare the planned site indicated in the indicator image with the site indicated in the indicator image, where the biopsy was performed or where the radiation source was introduced, and to update the provided treatment plan based on the comparison. The biopsy or brachytherapy can then be continued with the updated treatment plan. This can lead to a further improved accuracy of the biopsy or brachytherapy procedure.

In a further aspect of the present invention, an imaging method for imaging an introduction element within a living being is presented, wherein the introduction element is adapted to be inserted into the living being for performing a biopsy of an inner part of the living being or for introducing a radiation source into or next to the inner part of the living being for performing a brachytherapy, wherein the introduction element comprises at least one ultrasound receiver arranged at a known location of the introduction element, wherein the imaging method comprises:

emitting ultrasound signals for acquiring ultrasound data of the inner part of the living being by using an ultrasound probe for being inserted into the living being, tracking the location of the introduction element within the living being based on a reception of the emitted ultrasound signals by the at least one ultrasound receiver by using a first tracking unit, providing a pre-interventional image showing the inner part of the living being, which indicates a diseased condition of the inner part of the living being, by using an image providing unit, generating an indicator image showing the inner part of the living being and an indicator of the introduction element, based on the tracked location of the introduction element by using an imaging unit, wherein the imaging unit generates an ultrasound image showing the inner part of the living being based on the acquired ultrasound data and registers the pre-interventional image with the ultrasound image, wherein the imaging unit generates the indicator image such that it represents the ultrasound image or the registered pre-interventional image or a fused image of the ultrasound image and the registered pre-interventional image, wherein a site where the biopsy was performed or where the radiation source was introduced by means of the introduction element is indicated in the indicator image, and displaying the generated indicator image by using a display.

In a further aspect of the present invention, an imaging computer program for imaging an introduction element within a living being is presented, wherein the introduction element is adapted to be inserted into the living being for performing a biopsy of an inner part of the living being or for introducing a radiation source into or next to the inner part of the living being for performing a brachytherapy, wherein the introduction element comprises at least one ultrasound receiver arranged at a known location of the introduction element, wherein the imaging computer program comprises program code means for causing an imaging apparatus to carry out the steps of the imaging method as defined in claim 1, when the imaging computer program is run on a computer controlling the imaging apparatus.

It shall be understood that the imaging apparatus of claim 3, the imaging method of claim 1, and the imaging computer program of claim 8 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
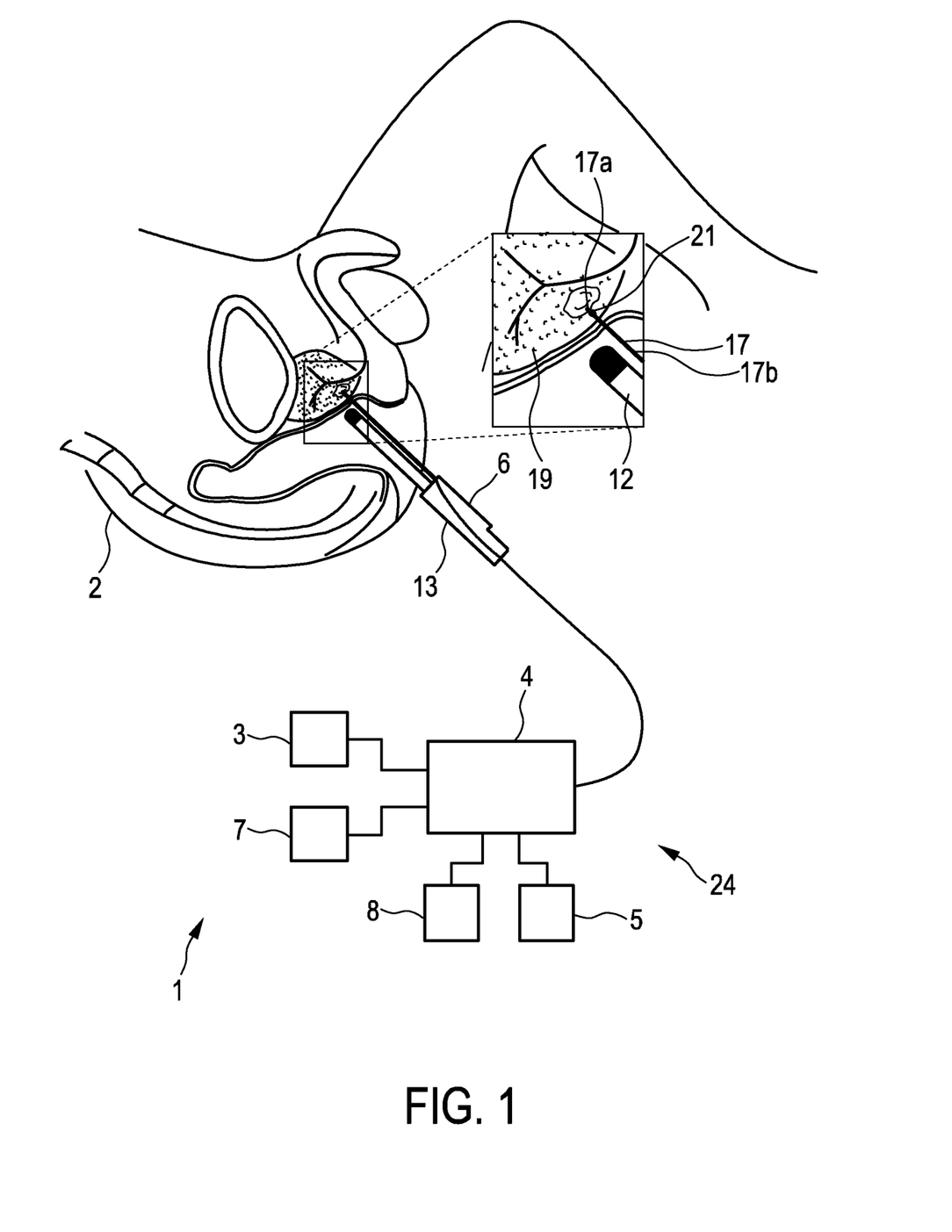
FIG. 1 shows schematically and exemplarily an embodiment of a system for performing a biopsy.

FIG. 1 shows schematically and exemplarily an embodiment of a system 1 for performing a biopsy. The system 1 comprises an introduction element 17, here, a needle, which is adapted to be inserted into a human 2 for performing a biopsy of the prostate 19 of the human 2. The needle 17 is an elongated element having a needle tip 17a and an elongated needle body 17b and comprises an ultrasound receiver 21 arranged at a known location of the needle 17, in this example, the needle tip 17a. During the biopsy, an imaging apparatus 24 is used to image the needle 17 within the human 2.

The imaging apparatus 24 comprises an ultrasound probe 12, here, a transrectal ultrasound probe, for being inserted into the human 2, wherein the ultrasound probe 12 is adapted to emit ultrasound signals for acquiring ultrasound data of the prostate 19 of the human 2, a first tracking unit 3 for tracking the location of the needle 17 within the human 2 being based on a reception of the emitted ultrasound signals by the ultrasound receiver 21, an imaging unit 4 for generating an indicator image showing the prostate 19 of the human 2 and an indicator of the needle 17 based on the tracked location of the needle 17, and a display 5 for displaying the indicator image. The first tracking unit can be implemented as described by Mung J. et al in "A Non-disruptive Technology for Robust 3D Tool Tracking for Ultrasound-Guided Interventions", MICCAI 2011, Part I, LNCS 6891, pp. 153-160, 2011, hereby incorporated by reference.

In this embodiment, the imaging apparatus 24 comprises an image providing unit 8 for providing a pre-interventional 3D image showing the prostate 19 of the human 2, which indicates a possible occurrence of cancer of the prostate 19 of the human 2, wherein the imaging unit 4 is adapted to generate a 3D ultrasound image showing the prostate 19 of the human 2 based on the acquired ultrasound data and to register the pre-interventional 3D image with the 3D ultrasound image. In this example, the pre-interventional 3D image is a 3D image that was generated before performing the biopsy using magnetic resonance imaging (MRI), which provides an enhanced delineation of cancer compared to ultrasound.

Here, the ultrasound probe 12 is a 2D ultrasound probe, i.e., e.g., a 1D array of ultrasound transducers (not shown in the figures), for acquiring ultrasound data of a 2D region. The imaging unit 4, in this case, is adapted to generate the 3D ultrasound image from successively acquired ultrasound data of a plurality of 2D regions using a 3D image reconstruction. In this example, it is foreseen that the user performs a freehand sweep of the 2D ultrasound probe 12 in order to successively acquire ultrasound data of the whole prostate 19 of the human 2, wherein the imaging unit 4 is adapted to reconstruct the 3D ultrasound image from the ultrasound data acquired during the freehand sweep.

The imaging apparatus 24, in this embodiment, comprises an introduction element guide 6, here, a needle guide, for guiding the needle 17, wherein the needle guide 6 is adapted to be attached to the ultrasound probe 12, here, the 2D ultrasound probe, and a second tracking unit 7 for tracking the location of the needle guide 6. The imaging unit 4 is adapted to further use the tracked location of the needle guide 6 in the 3D image reconstruction. Here, the tracking of the location of the needle guide 6 by the second tracking unit 7 is based on an electromagnetic (EM) tracking by making use of appropriate EM sensors mounted on the needle guide 6. In other embodiments, however, another suitable tracking technology may be used.

Figure 2:
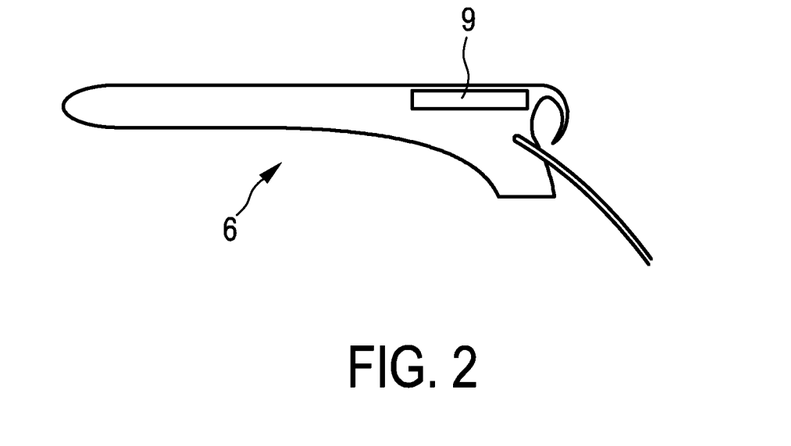
FIG. 2 shows schematically and exemplarily an embodiment of a needle guide to be used with the system shown in FIG. 1.

An embodiment of a needle guide 6 to be used with the system 1 shown in FIG. 1 is schematically and exemplarily shown in FIG. 2. The needle guide 6 is adapted to be attached to the ultrasound probe 12, in particular, to a handle 13 (shown in FIG. 1) of the ultrasound probe 12. A channel 9 allows the needle 17 to be inserted and to be moved back and forth along an axis extending in a longitudinal direction of the needle guide 6.

Referring back to FIG. 1, the needle guide 6 is adapted for guiding the needle 17 within the 2D region, i.e., the 2D region of which the 2D ultrasound probe 12 acquires ultrasound data, wherein the first tracking unit 3 is adapted to track the location of the needle 17 within the 2D region.

Here, the imaging unit 4 is adapted to generate as the indicator image a 2D image, wherein the 2D image is generated from the currently acquired ultrasound data, wherein the tracked location of the needle 17 is indicated in the 2D image, wherein the display 5 is adapted to display the 2D image. Additionally or alternatively, however, the imaging unit 4 can also be adapted to determine a slice within the human 2 corresponding to the 2D region based on the tracked location of the needle guide 6 and to generate as the indictor image a slice image of the determined slice, wherein the slice image is generated from the registered pre-interventional 3D image or as a fused image from the registered pre-interventional 3D image and the currently acquired ultrasound data, wherein the tracked location of the needle 17 is indicated in the slice image, wherein the display 5 is adapted to display the slice image.

In this embodiment, the tracked location of the needle 17 is the location of the needle tip 17a at which the ultrasound receiver 21 is arranged. The tracked location of the needle tip 17a can be indicated in the 2D image or the slice image by means of some visual mark that shall represent the needle tip 17a, e.g., a colored dot, a crosshair, et cetera.

The imaging unit 4, here, is further adapted to generate as the indicator image a 3D image, wherein the 3D image represents the 3D ultrasound image or the registered pre-interventional 3D image or a fused image of the 3D ultrasound image and the registered pre-interventional 3D image, wherein a site where the biopsy was performed by means of the needle 17 is indicated in the 3D image, wherein the display 5 is adapted to display the 3D image.

For instance, the tracked location of a biopsy needle can be stored at the time, at which the biopsy is taken, wherein this stored location can be regarded as being the site where the biopsy was performed and wherein this site can be indicated in the 3D image. Thus, a marker can be provided, which indicates the precise location where the biopsy was taken. This marker may be shown in a pre-operative image, i.e. in the pre-interventional 3D image, in an intra-operative image, i.e. in the 3D ultrasound image, and/or in the fused image. The pre-interventional 3D image can comprise an indicator for indicating a planned site, at which, according to a treatment plan, the biopsy should have been performed. Therefore, if the site where the biopsy was performed, i.e. the actual biopsy location, is indicated in the pre-interventional 3D image or in the fused image, the actual biopsy location can directly be compared with the corresponding planned location. In particular, the treatment plan can be updated based on the actual biopsy location, if a comparison of the actual biopsy location with the planned biopsy location indicates a difference which requires an update of the treatment plan. For instance, if the comparison between the actual biopsy location and the planned biopsy location reveals that at a planned biopsy location a biopsy has not been taken or not completely been taken, i.e. from a planned biopsy region only a part has been taken, the treatment plan can be updated such that a planned biopsy location indicated in the updated treatment plan covers the previously planned biopsy region, at which a biopsy has not been taken, although this should have been done. The provision of an initial treatment plan indicating a planned site, at which a biopsy should be performed, the comparison of the planned site indicated in the provided treatment plan and in the 3D image with the site indicated in the 3D image, where the biopsy was actually performed, and the updating of the provided treatment plan based on the comparison can be performed by a treatment plan providing unit 25.

Since the planned site can be indicated in the 3D image, wherein the planned site is defined by the treatment plan, and since also the tracked location of the introduction element is indicated in the 3D image, the biopsy or the introduction of the radiation source can simply be guided, i.e. performed, in accordance with the treatment plan. The treatment plan can initially have been made based on the pre-interventional 3D image, which might be a computed tomography image or a magnetic resonance image, particularly a magnetic resonance spectroscopy image, by, for instance, marking one or several sites in the pre-interventional 3D image, which should be treated. The treatment plan can also be determined based on other information like elastography information, a cancer atlas, et cetera. The treatment plan may be determined automatically, manually or semi-automatically, wherein a clinical decision support (CDS) system may be used. The post-operative histo-pathology, i.e. the site where the biopsy was performed or, in case of brachytherapy, where the radiation source was introduced, can be correlated to CDS data like the pre-interventional 3D image, a planned site, statistical atlases that might be registered with the 3D image, et cetera. Generally, the information provided by the sites where the biopsy was performed or where the radiation source was introduced indicated in the 3D image can be used, if a repeat interventional procedure like a repeat biopsy should be conducted. The post-interventional location information can act as additional pre-operative information to be used for a further invention.

Figure 4:
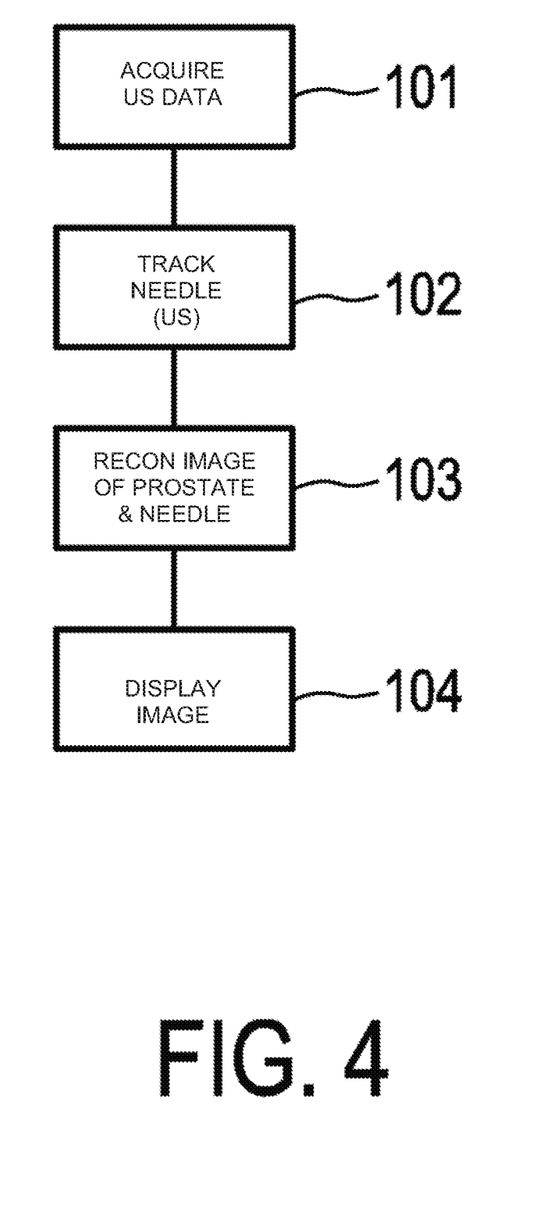
FIG. 4 shows a flowchart exemplarily illustrating an embodiment of an imaging method to be used with the system shown in FIG. 1.

In the following, an embodiment of an imaging method for imaging an introduction element 17, here, a needle, within a human 2 will be described with reference to the exemplary flowchart shown in FIG. 4. The needle 17 is adapted to be inserted into the human 2 for performing a biopsy of the prostate 19 of the human 2. As explained above with reference to FIG. 1, the needle 17 is an elongated element having a needle tip 17a and an elongated needle body 17b and comprises an ultrasound receiver 21 arranged at a known location of the needle 17, in this example, the needle tip 17a.

In step 101, after the ultrasound probe 12 has been inserted into the human 2, the ultrasound probe 12 emits ultrasound signals for acquiring ultrasound data of the prostate 19 of the human 2. In step 102, the first tracking unit 3 tracks the location of the needle 17 within the human 2 based on a reception of the emitted ultrasound signals by the ultrasound receiver 21. In step 103, the imaging unit 4 generates an indicator image showing the prostate 19 of the human and an indication of the needle 17 based on the tracked location of the needle 17. In step 104, the display 5 displays the generated indicator image.

Figure 3:
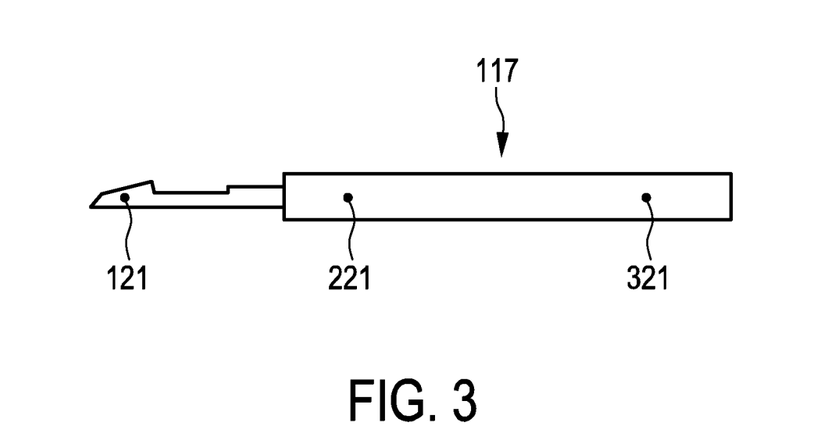
FIG. 3 shows schematically and exemplarily an embodiment of a needle comprising multiple ultrasound receivers arranged at known locations of the needle.

Although in the embodiment of the system 1 for performing a biopsy described with reference to FIG. 1 the needle only comprises a single ultrasound receiver 21 arranged at the needle tip 17a, also multiple ultrasound receivers may be foreseen. For example, FIG. 3 shows schematically and exemplarily an embodiment of a needle 117 comprising multiple, here, three, ultrasound receivers 121, 221 and 321 arranged at known locations of the needle 117. With such a configuration, it can be possible to track the location of the whole needle 117 based on the reception of the emitted ultrasound signals by the multiple ultrasound receivers 121, 221 and 321. The tracked location of the needle 117 can then be indicated in the 2D image or the slice image by means of some visual mark that shall represent the needle 117, e.g., a colored line, et cetera. This can also allow to accurately visualize situations in which the needle 117 bends and deflects from its original straight path.

In the embodiment of the system 1 for performing a biopsy described with reference to FIG. 1 it is foreseen that the user performs a freehand sweep of the 2D ultrasound probe 12. Alternatively, it can also be foreseen that the user rotates the 2D ultrasound probe 12 around an axis directed towards the prostate 19 of the human 2 in order to successively acquire sufficient ultrasound data of the prostate 19 of the human 2 for allowing a 3D image reconstruction. In some embodiments, it can even be foreseen that the 2D ultrasound probe 12 comprises driving means (not shown in the figures), e.g., comprising an electrical motor or the like, that are adapted to perform a respective sweep or rotation of the ultrasound transducers.

Although in the embodiment of the system 1 for performing a biopsy described with reference to FIG. 1 the ultrasound probe 12 is a 2D ultrasound probe, the ultrasound probe 12 can also be a 3D ultrasound probe, i.e., e.g., a 2D array of ultrasound transducers, for acquiring ultrasound data of a 3D region. For example, if the 3D region of which the ultrasound data is acquired within the living being is sufficiently large, the 3D ultrasound image can preferentially be generated from a single acquisition of ultrasound data.

If the ultrasound probe 12 is a 3D ultrasound probe, the first tracking unit 3 is adapted to track the location of the needle 17 within the 3D region. The imaging unit 4 can then be adapted to determine a slice within the 3D region including the tracked location of the needle 17 and to generate as the indicator image a slice image of the determined slice, wherein the slice image is generated from the currently acquired ultrasound data, wherein the tracked location of the needle 17 is indicated in the slice image, wherein the display 5 is adapted to display the slice image. Additionally or alternatively, however, the imaging unit 4 can also be adapted to determine a slice within the human 2 including the tracked location of the needle 17 based on the tracked location of the needle 17 and the tracked location of the needle guide 6 and to generate as the indictor image a slice image of the determined slice, wherein the slice image is generated from the registered pre-interventional 3D image or as a fused image from the registered pre-interventional 3D image and the currently acquired ultrasound data, wherein the tracked location of the needle 17 is indicated in the slice image, wherein the display 5 is adapted to display the slice image.

Although in FIG. 1 only a single introduction element is shown, also several introduction elements, e.g., a needle and one or more catheters, can be inserted into the human. Moreover, although in the above described embodiments, the living being is a human, in other embodiments the living being can also be an animal, and, although in the above described embodiments the introduction element is introduced for performing a biopsy of the prostate, the introduction element can also be introduced for performing a biopsy of another part of the living being, especially of another organ.

Although the present invention has been described above with reference to embodiments of a system for performing a biopsy, in other embodiments a system for performing a brachytherapy may be foreseen. In this case, the introduction element is preferentially adapted to be inserted into a living being for introducing a radiation source into or next to an inner part of the living being.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the tracking of the location of the introduction element within the living being, the generation of the 3D ultrasound image, the registration of the pre-interventional 3D image with the 3D ultrasound image, the generating of the indicator image showing the inner part of the living being, et cetera, performed by one or several units or devices can be performed by any other number of units or devices. For example, the first tracking unit can be integrated into the imaging unit such that the imaging unit tracks the location of the introduction element within the living being. The operations and/or the control of the imaging apparatus in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging apparatus for imaging an introduction element like a needle or a catheter for performing a biopsy or a brachytherapy. The introduction element comprises at least one ultrasound receiver arranged at a known location thereof. An ultrasound probe for being inserted into a living being emits ultrasound signals for acquiring ultrasound data of an inner part of the living being. A first tracking unit tracks the location of the introduction element being based on a reception of the emitted ultrasound signals by the at least one ultrasound receiver, an imaging unit generates an indicator image showing the inner part and an indicator of the introduction element, based on the tracked location, and a display displays the indicator image. This allows receiving a feedback about the location of the introduction element.

The invention claimed is:

1. An imaging method for imaging an introduction element within a living being, wherein the introduction element is adapted to be inserted into the living being for performing a biopsy of an inner part of the living being or for introducing a radiation source into or next to the inner part of the living being for performing a brachytherapy, wherein the introduction element comprises at least one ultrasound receiver arranged at a known location of the introduction element, wherein the imaging method comprises:
   emitting ultrasound signals for acquiring ultrasound data of the inner part of the living being by using an ultrasound probe inserted into the living being, wherein the ultrasound probe is a 3D ultrasound probe for acquiring ultrasound data of a 3D region of the living being,
tracking the location of the introduction element within the 3D region of the living being based on a reception of the emitted ultrasound signals by the at least one ultrasound receiver,
receiving a pre-interventional image of the 3D region of the inner part of the living being,
tracking the location of an introduction element guide which is attached to the ultrasound probe and which is configured to guide the introduction element,
generating an indicator image of the 3D region of the inner part of the living being including an indicator of the tracked location of the introduction element including:
reconstructing an ultrasound image of the 3D region of the inner part of the living being from the acquired ultrasound data,
registering the pre-interventional 3D image with the ultrasound image,
indicating a site where the biopsy was performed or where the radiation source was introduced by the introduction element in the indicator image,
determining a slice of the 3D region of the living being which includes a current location of the introduction element and the tracked location of the introduction element guide,
wherein the indicator image is a slice image of the determined slice,
wherein the slice image is generated from the registered pre-interventional 3D image or a fused image of the registered pre-interventional 3D image and a currently generated ultrasound image,
indicating the location of the introduction element in the indicator image, and
controlling a display device to display the indicator image.

2. The method as defined by claim 1 further including:
sliding the introduction element axially relative to the introduction element guide.

3. An imaging apparatus comprising:
a 3D ultrasound probe configured to be inserted into a living being, the 3D ultrasound probe being configured to emit ultrasound signals into a 3D region of an inner part of the living being and acquire ultrasound image data from the 3D region;
an introduction element configured to be inserted into the living being and being configured to (1) introduce a radiation source into or next to the inner part of the living being for performing brachytherapy, or (2) perform a biopsy on the inner part of the living being;
at least one ultrasound receiver attached at a known location to the introduction element and configured to generate a tracking electrical signal indicative of a location of the ultrasound receiver in the 3D region of the inner part of the living being in response to receiving the ultrasound signals emitted by the ultrasound probe;
a guide attached to the ultrasound probe and configured to guide the introduction element;
a guide tracker configured to track a location of the guide;
one or more computer processors configured to:
receive a pre-intervention 3D image of the 3D region of the inner part of the living being,
reconstruct a 3D ultrasound image of the 3D region of the inner part of the living being from the acquired ultrasound image data,
register the pre-intervention 3D image with the 3D ultrasound image to form a registered 3D ultrasound image,
determine a location of the introduction element in the 3D region of the inner part of the living being from the tracking electrical signal and indicate the location of the introduction element in the registered 3D ultrasound image,
indicate a site in the registered 3D ultrasound image where a biopsy was performed or where the radiation source was introduced,
determine a location of the guide in the registered 3D region of the inner part of the living being,
determine a slice image in the 3D region of the inner part of the living being indicating the determined location of the introduction element in one of the registered 3D image or a fused pre-interventional 3D image with a current ultrasound image based on the determined locations of the ultrasound receiver and the guide, and
control a display device to display the slice image.

4. The imaging apparatus as defined in claim 3, wherein the introduction element includes a needle and the guide includes a channel configured to slidably receive the needle for movement back and forth along an axis of the needle.

5. The imaging apparatus as defined in claim 3, wherein the one or more computer processors are further configured to indicate a planned site, at which a biopsy should be performed or where the radiation source should be introduced, in the slice image.

6. The imaging apparatus as defined in claim 3, wherein the introduction element is a needle or a catheter.

7. The imaging apparatus as defined in claim 3, wherein the inner part of the living being is the prostate of the living being, wherein the ultrasound probe is a transrectal ultrasound probe.

8. A non-transitory computer medium carrying a computer program for causing the one or more processors to control an imaging apparatus as defined in claim 3 to carry out the steps of:
emitting ultrasound signals for acquiring ultrasound data of an inner part of a living being by using an ultrasound probe inserted into the living being, wherein the ultrasound probe is a 3D ultrasound probe for acquiring ultrasound data of a 3D region of the living being,
tracking a location of an introduction element within a 3D region of the living being based on a reception of the emitted ultrasound signals by at least one ultrasound receiver on the introduction element,
receiving a pre-interventional image of the 3D region of the inner part of the living being,
tracking a current location of an introduction element guide which is attached to the ultrasound probe and configured to guide the introduction element,
generating an indicator image of the 3D region of the inner part of the living being including an indicator of the tracked location of the introduction element including:
reconstructing an ultrasound image of the 3D region of the inner part of the living being from the acquired ultrasound data,
registering the pre-interventional 3D image with the ultrasound image, indicating a site where the biopsy was performed or where the radiation source was introduced by the introduction element in the indicator image, determining a slice of the 3D region of the living being which includes the current location of the introduction element and the tracked location of the introduction element guide, wherein the indicator image is a slice image of the determined slice, wherein the slice image is generated from the registered pre-interventional 3D image or a fused image of the registered pre interventional 3D image and a currently generated ultrasound image, indicating the location of the introduction element in the indicator image, and controlling a display device to display the indicator image.

* * * * *